US009907806B2

(12) United States Patent
Lindenthal et al.

(10) Patent No.: US 9,907,806 B2
(45) Date of Patent: *Mar. 6, 2018

(54) PHARMACEUTICAL COMPOSITION FOR EMERGENCY CONTRACEPTION

(71) Applicant: Bayer Intellectual Property GmbH, Monheim (DE)

(72) Inventors: Bernhard Lindenthal, Berlin (DE); Rolf Schürmann, Teltow (DE); Sascha General, Berlin (DE)

(73) Assignee: BAYER INTELLECTUAL PROPERTY, GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/569,579

(22) Filed: Dec. 12, 2014

(65) Prior Publication Data

US 2015/0105359 A1 Apr. 16, 2015

Related U.S. Application Data

(63) Continuation of application No. 13/377,809, filed as application No. PCT/EP2010/003497 on Jun. 10, 2010, now Pat. No. 8,921,345.

(30) Foreign Application Priority Data

Jun. 23, 2009 (DE) ........................ 10 2009 030 607

(51) Int. Cl.
*A61K 31/57* (2006.01)
*A61K 31/405* (2006.01)
*A61K 31/196* (2006.01)
*A61K 31/18* (2006.01)
*A61K 31/192* (2006.01)
*A61K 31/415* (2006.01)
*A61K 31/5415* (2006.01)
*A61K 31/542* (2006.01)
*A61K 31/567* (2006.01)
*A61K 31/575* (2006.01)
*A61K 31/585* (2006.01)
*A61K 45/06* (2006.01)

(52) U.S. Cl.
CPC .............. *A61K 31/57* (2013.01); *A61K 31/18* (2013.01); *A61K 31/192* (2013.01); *A61K 31/196* (2013.01); *A61K 31/405* (2013.01); *A61K 31/415* (2013.01); *A61K 31/542* (2013.01); *A61K 31/5415* (2013.01); *A61K 31/567* (2013.01); *A61K 31/575* (2013.01); *A61K 31/585* (2013.01); *A61K 45/06* (2013.01)

(58) Field of Classification Search
None
See application file for complete search history.

(56) References Cited

U.S. PATENT DOCUMENTS

| 6,086,909 A | 7/2000 | Harrison et al. |
| 2004/0058975 A1* | 3/2004 | Lindenthal ........... A61K 31/365 514/406 |
| 2012/0172343 A1 | 7/2012 | Lindenthal et al. |
| 2016/0000805 A1 | 1/2016 | Lindenthal et al. |

FOREIGN PATENT DOCUMENTS

| WO | 9731631 A1 | 9/1997 |
| WO | 03/045397 A1 | 6/2003 |
| WO | 2010149273 A1 | 12/2010 |

OTHER PUBLICATIONS

Massai et al. in Human Reproduction 22(2), 434-439 (2007).*
Lindenthal et al. in US 2004/0058975 (published: Mar. 25, 2004).*
Croxatto et al. in Contraception 442-450 (2004).*
"Postinor-2" in www.nps.org.au/medicines/contraceptive-methods/progestogen-only-contraceptives/levonrgestrel-progestogen-only-contraceptives/postinor-2-tablets (retrieved from the internet (Dec. 9, 2013).*
Kadoch, I.J. in Reproductive BioMedicine Online 16(2) 245-249 (2008).*
Blanco et al. in J. Rheumatol. 26(6):1366-73 (1999) (Abstract).*
Akil et al, "Infertility May Sometimes be Assosicated with NSAID Consumption," British Journal of Rheumatology, 1996, 35:76-78.
Atken et al., As the World Grows: Contraception in the 21st Century, Journal of Clinical Investigation, Apr. 2008, 118 (4):1330-1343.
Bazin et al. "Effect of nomegestrol acetate, a new 19 nor-progesterone derivative, on pituitary-ovarian function in woman," Br J Obstet Gynaecol 1987, 1987, 94, 1199-1204.
Croxatto et al., "Effects of the Yuzpe regiman, given during the follicular phase, on ovarian function," Contraception 2002, 65:121-8.
Croxatto et al., "Mechanism of action of hormonal preparations used for emergency contraception: a review of the literature," Contraception 2001, 63:111-21.
Croxatto et al., "Mechanisms of action of emergency contraception," Steroids 2003;68:1095-8.
Davidoff et al., "Plan B and the politics of doubt," J Am Med Assoc 2006, 296(14):1775-8.
Diao et al., "Rat ovulation, implantation and decidualization can be severely compromised by COX-2 inhibitors," Frontiers in Bioscience 12, May 1, 2007, 3333-3342.
Druckmann et al., "Profile of the progesterone derivative chlormadinone acetate-Pharmocodynamic properties and therapeutic applications," Contraception 79 (2009) 272-281.
Duffi et al, "Follicular administration of cyclooxygenase inhibitor can prevent oocyte relase without alteration of normal luteal function in rhesus monkeys," Human Reproduction 2002, 17(11):2825-2831.
Durand et al., "Late follicular phase administration of levonorgestrel as an emergency contraceptive changes the secretory pattern of glycodelin in serum and endometrium during the luteal phase of the menstrual cycle," Contraception 2005, 71:451-7.

(Continued)

*Primary Examiner* — Dennis Heyer
(74) *Attorney, Agent, or Firm* — Nixon & Vanderhye P.C.

(57) ABSTRACT

The invention relates to pharmaceutical compositions for emergency contraception, to the use of levonorgestrel in combination with COX inhibitors for the preparation of pharmaceutical compositions for the stated purpose, and to a method for preparing these pharmaceutical compositions.

5 Claims, No Drawings

(56) References Cited

OTHER PUBLICATIONS

Glasier, Anna, "Emergency postcoital contraception," N Engl J Med, Oct. 9, 1997, 337:1058-64.
Hapangama et al., "The effects of peri-ovulatory administration of levonorgestrel on the menstrual cycle," Contraception 2001, 63:123-9.
Kesserü et al., "The hormonal and peripheral effects of d-norgestrel in postcoital contraception," Contraception 1974, 10(4):411-24.
Kubba et al., "The biochemistry of human endometrium after two regimens of postcoital contraception: a dl-norgestrel/ ethinylestradiol combination or danazol," Fertil Steril, Apr. 1986, 45(4):512-6.
Lim et al., "Multiple Female Reproductive Failures in Cyclooxygenase 2-Deficient Mice"; Cell, Oct. 17, 1997, 91:197-208.
Ling et al., "Mode of action of dl-norgestrel and ethinylestradiol combination in postcoital contraception," Fertil Steril 1979, 32:297-302.
Ling et al., "Mode of action of dl-norgestrel and ethinylestradiol combination in postcoital contraception. II. Effect of postovulatory administration on ovarian function and endometrium," Fertil Steril 1983, 39(3):292-7.
Marions et al., "Effect of emergency contraception with levonorgestrel or mifepristone on ovarian function," Contraception 2004, 69:373-7.
Marions et al., "Emergency contraception with mifepristone and levonorgestrel: mechanism of action," Obstet Gynecol, Jul. 2002, 100(1):65-71.
Moore, et al., "Influence of dienogest on ovulation in young fertile women," Clin Drug Invest, Oct. 1999, 18(4):271-8.
Müller et al,. "Postcoital treatment with levonorgestrel does not disrupt postfertilization events in the rat," Contraception 2003, 67:415-19.
Nascimento et al., "In vivo assessment of the human sperm acrosome reaction and the expression of glycodelin-A in human endometrium after levonorgestrel-emergency contraceptive pill administration," Hum Reprod 2007, 22 (8):2190-5.
Okewole et al., "Effect of single administration of levonorgestrel on the menstrual cycle," Contraception 2007, 75:372-7.
Ortiz et al., "Postcoital administration of levonorgestrel does not interfere with post-fertilization events in the new-world monkey *Cebus apella*," Hum Reprod 2004, 19(6)1352-6.
Pall et al, "Introduction of delayed follicular rupture in the human by the selective COX-2 ihibitor rofecoxib: A randomized double-blind study"; Human Reproduction, 2001, 16(7):1323-1328.
Raymond et al., "Effect of the Yuzpe regimen of emergency contraception on markers of endometrial receptivity," Hum Reprod 2000, 15(11)2351-5.
Rowlands et al, "A possible mechanism of action of danazol and an ethinylestradiol/norgestrel combination used as postcoital contraceptive agents," Contraception 1986, 33:539-45.
Sirois et al., "Cyclooxygenase-2 and its role in ovulation: A 2004 account"; Human Reproduction Update, 2004, 10(5): 373-385.
Sookvanichsilp et al., "Anti-implantaion effects of indomethacin and celecoxib in rats, " Contraception, May 2002, 65:373-378.
Swahn et al., "Effect of post-coital contraceptive methods on the endometrium and the menstrual cycle," Acta Obstet Gynecol Scand 1996; 75:738-44.
Taskin et al., "High doses of oral contraceptives do not alter endometrial $\alpha 1$ and $\alpha v\beta 3$ integrins in the late implantation window," Fertil Steril 1994, 61(5):850-5.
Teichmann et al. „Empfängnishütung: eine vergleichende Übersicht aller Methoden, Risiken und Indikationen, erschienen im Georg Thieme Verlag (1996), pp. 23-24.
Trussell et al., "Statistical evidence concerning the mechanism of action of the Yuzpe regimen of emergency contraception," Obstet Gynecol 1999, 93(5):872-6.
Yuzpe et al., "Post coital contraception—a pilot study," J Reprod Med 1974, 13(2):53-8.
Ling et al., "Mode of action of dl-norgestrel and ethinylestradiol combination in postcoital contraception. III. Effect of preovulatory administration following the luteinizing hormone surge on ovarian steroidogenesis," Fertil Steril 1983, 40:631-6.
U.S. Appl. No. 14/647,740, 371(c) date May 27, 2015, published as US 2016-0000805 on Jan. 7, 2016.
Salhab et al., "Further investigation on meloxicam contraceptivity in female rabbits: Luteinizing unruptured follicles, a microscopic evidence," Contraception, Jun. 2003, 67(6): 485-489.
Herkert et al., "The progestin levonorgestrel induces endothelium-independent relaxation of rabbit jugular vein via inhibition of calcium entry and protein kinase C: role of cyclic AMP," British Journal of Pharmacology, Aug. 2000, 130(8): 1911-1918.
Lau et al., "Pregnancy blockade by indomethacin, an inhibitor of prostaglandin synthesis: Its reversal by prostaglandins and progesterone in mice," Prostaglandins, Dec. 1, 1973, 4(6): 795-803.

* cited by examiner

PHARMACEUTICAL COMPOSITION FOR EMERGENCY CONTRACEPTION

The invention relates to pharmaceutical compositions for emergency contraception (also known as the "day after pill"), to the use of levonorgestrel in combination with COX inhibitors for the preparation of pharmaceutical compositions for the stated purpose, and to a method for preparing these pharmaceutical compositions.

Various devices and pharmaceutical compositions, for example the condom, pessary, intrauterine pessary and the various monophasic or multiphasic oral contraceptives, are available for preventing unwanted pregnancy. However, despite the wide variety of methods of contraception, sexual intercourse is in many cases performed entirely without protection, even when pregnancy is not wanted.

Such a situation arises, for example, in rape cases or when the contraceptive device, e.g. condom, is damaged. If ovulation is prevented in these cases, or if fertilization is prevented once ovulation has taken place, then pregnancy can be avoided. For this purpose, emergency contraception has to performed soon after sexual intercourse, at the latest within 72 hours.

This type of emergency contraception can be performed not only by intrauterine contraception with copper-containing intrauterine pessaries (e.g. Nova T®), but also in particular using emergency contraceptive pills (ECPs), where a distinction is made between two types: (a) EPCs that contain both estrogens and also gestagens, and (b) the more recent "progestin only" pills, which contain only gestagen as the active constituent.

The more recent "progestin only" ECPs have by now largely supplanted the older combined ECPs, since they are more efficient and cause fewer side effects. However, the contraceptive efficacy of these preparations too is considerably below the efficacy that is achieved by regular administration of an oral contraceptive. Thus, in an article entitled "Understanding Contraceptive Failure" [Best Practice & Research Clinical Obstetrics and Gynaecology 23 (2009) 199-209], Trussel et al. report that, in different studies, the effectiveness of LNG-based EPCs was only between 59 and 94%.

The mechanism of action of these preparations containing estrogen and gestagen, and also of the preparations that exclusively contain gestagen, has been investigated in a large number of studies. These studies confirm that the mechanism of action lies in ovulation being inhibited or delayed[1,2,3,4].

This delay in ovulation explains the efficacy of ECPs if they are taken during the first half of the cycle, i.e. before ovulation.

Studies have also examined the question of whether EPCs have an effect on avoiding pregnancy even after ovulation. A comprehensive review of this question is provided by J. Trussell and E. G. Raymond in their article "Emergency Contraception: A Last Chance to Prevent Unintended Pregnancy" published in March 2009. However, in view of the different and in some cases contradictory (study) results, the authors come to the conclusion that the question of whether ECPs can prevent pregnancy even after fertilization will never be resolved.

Thus, some studies indicate histological or biochemical changes in the endometrium after treatment with ECPs. These studies permit the conclusion that ECPs may also interfere with the nidation of the fertilized egg in the endometrium[1,5,6,7].

More recent studies, however, contradict this assumption that the administration of ECPs has effects on the endometrium[1,8,9].

Further effects that are discussed include a disturbance in the function of the corpus luteum, thickening of the cervical mucosa, which affects the entry of sperm, a change in the tubal transport of sperm and egg, and the direct inhibition of fertilization[13,10,11,12].

However, statistical data concerning the efficacy of ECPs indicate that various factors contribute to the efficacy, and their effect is not attributable solely to the delay or prevention of ovulation[14].

Some studies have shown that early treatment with ECPs that contain only the gestagen (levonorgestrel) has an effect both on the ovulatory process and also on luteal function[15,18,19,20,58]. By contrast, two other studies show no effect on the endometrium[16,17].

Another study, in which the gestagen (levonorgestrel) was administered before the LH surge, in turn shows an effect on the secretory pattern of glycodelin in serum and endometrium[21]. However, this result could not be confirmed in a later study whose very purpose was to assess endometrial glycodelin expression[22].

A study of levonorgestrel carried out more than 30 years ago established an effect on the migration of the sperm and the function of the genital tract[23]. A more recent study indicated, however, that 1.5 mg of levonorgestrel has no effects on the cervical mucosa or on the entry of sperm into the uterine cavity[22].

The reduced efficacy of EPCs when their administration is delayed after unprotected sex suggests that EPCs have no effect on the nidation of the oocyte, since otherwise the efficacy of the product would probably not be dependent on the time it was administered, at least as long as the ECP is taken before nidation[24].

Studies on rats and capuchin monkeys (Cebus) with levonorgestrel in an ovulation-inhibiting dose show that fertility is not impaired after fertilization[12,25,26]. However, it is unclear whether this observation can be applied to humans.

Although the mechanism of action of ECPs is not entirely clear, it has been demonstrated that ECPs have no abortive effect, even within the meaning of the definitions used by the medical authorities, e.g. the Food and Drug Administration/National Institutes of Health[27].

Besides the studies examining the mechanism of action, many studies have examined the suitability of different treatment regimens, gestagens and doses for post-coital contraception. Post-coital contraception means that women who do not wish to become pregnant after unprotected sex take suitable pharmaceutical products intended to prevent ovulation.

The first work in this connection was carried out as early as the 1970s. Thus, various gestagens, including levonorgestrel, were tested as routine post-coital contraceptives in extensive studies (The Journal of Reproductive Medicine, 13(2), (1974); Contraception, 7(5), 367-379, (1973); Reproduction, 2(1), 61-62, (1975); International Journal of Fertility, 20, 156-1 60, (1 975). The once a day doses were between 150 μg and 1,500 μg. The results of the studies showed that the post-coital contraceptive efficiency of levonorgestrel, when used alone, was low even at a dose of 1 mg.

A. A. Yuzpe and co-workers [The Journal of Reproductive Medicine 13(2), (1974)] reported the results of such studies in which a pharmaceutical composition containing 100 μg of ethinylestradiol and 1.0 mg of norgestrel was used as a post-coital contraceptive in a single dose. The composition was taken within five days after unprotected sex. This method was later modified. On the one hand, the period of time for possible use of the composition was reduced from 5 days to 72 hours, and, on the other hand, the dose was doubled in the sense that administration of the composition was repeated 12 hours after the first administration [Fertility and Sterility, 28, 932-936, (1977); ibid. 37, 508-51 3 (1982); International Journal of Gynaecology and Obstetrics, 15, 133-1 36, (1977)]. This modification improved the success of the method.

Following the studies by A. A. Yuzpe and co-workers, various other trials were conducted to demonstrate the efficacy of this combination. In these studies, the total dose of ethinylestradiol was 0.2 mg, combined with 2.0 mg of norgestrel or 1.0 mg of levonorgestrel. The results of the studies showed that, although the above administration (Yuzpe regimen) caused fewer side effects than estrogens which were used earlier at higher doses, the relative incidence of nausea and vomiting was still very high (50% and 20% respectively). These side effects are due to the estrogen effect and lead to reduced acceptance of the method. Moreover, the efficacy of the treatment decreases when vomiting occurs.

The use of levonorgestrel for emergency contraception was discovered in the 90s. The results of the studies were reported in two well documented publications [Lancet, 352, 428-433, (1998), and Human Reproduction, 8(3), 389-392, (1993)]. The efficacy of tablets which contain only 0.75 mg of levonorgestrel and of combination tablets from the Yuzpe method which contain 0.1 mg of ethinylestradiol and 1.0 mg of levonorgestrel was investigated within 48 hours and also within 72 hours after unprotected sex, with the second dose being administered 12 hours after the first one. The results showed that the protection with two tablets that contain 0.75 mg of levonorgestrel was better than the protection with the Yuzpe regimen, and also that the women who received only levonorgestrel experienced fewer side effects, a finding that could be attributed to the absence of ethinylestradiol.

The results of the clinical studies also showed that the earlier the treatment was started post coitus, the better the effect. However, experience shows that a woman will delay taking the first tablet in order to avoid a situation where the second dose to be taken after 12 hours falls at an unsuitable time (for example at a time when she will be asleep). According to the studies, however, exact observance of the 12-hour interval between the two doses is essential in order not to reduce the desired effect. According to statistical data, most of the women took the second dose within 12 to 16 hours after the first dose [Lancet, 352, 428-433, (1998)].

In view of the stated disadvantage (the delayed administration of the 2nd tablet), European patent 1448207 describes a product that comprises just one tablet but contains twice the amount of levonorgestrel, i.e. 1.5 mg of active substance. This tablet has to be taken within 72 hours after unprotected sex. As a clinical study was able to show, the contraceptive effect is comparable to, or even slightly better than, the contraceptive effect when the dose is divided into tablets, each containing 0.75 mg [E. Jonannson et al., Human Reproduction, vol. 17, no. 6, 1472-1476 (2002)]. Johannsen assumes, however, that the high-dose formulation of 1.5 mg will be more poorly tolerated (nausea, queasiness, vomiting, and also disturbance of the menstrual cycle).

Other research groups have investigated the influence of COX inhibitors on ovulation. For example, Pall et al. investigated the influence of rofecoxib on ovulation [Pall et al.; Human Reproduction vol. 16, no. 7, pp 1323-1328 (2001)]. In this study, 25 mg of the active substance were used on 9 successive days. A delay in ovulation of over 48 hours was obtained in 4 of 6 patients.

The study by M. S. Bata et al. is in line with Pall's results but investigates the influence of meloxicam on ovulation [Bata et al., J Clin Pharmacol (2006) 46:925-932]. This study shows that, with a dose of 30 mg per patient and day (on 5 successive days), it is possible to achieve a delay in ovulation of 5 days.

Although COX inhibitors are known in principle as being relatively well tolerated, the EMEA [EMEA/62838/2005; EMEA/62757/2005] points to this class of substances as posing a higher risk of adverse cardiovascular events, and it therefore recommends that the lowest effective dose be used. The currently available study data show a trend whereby the risk of renal and cardiovascular events increases as the selectivity for COX-2 (cyclooxygenase type 2) increases. Meloxicam should therefore be treated with circumspection compared to other COX inhibitors such as piroxicam [Clin Pharmacol Ther. 2009 February; 85(2):190-7; Pharmacotherapy 2006; 26(7):919-938]. Increasing COX-2 selectivity, however, is linked with lesser gastro-intestinal side effects, and the adverse cardiovascular events have hitherto been found only in cases of chronic use [Am. J. Med. 2004; 117:100-106].

In a pilot study, Massai et al. investigated the use of meloxicam in combination with levonorgestrel (LNG) on the ovulation point in connection with emergency contraception [Human Reproduction vol. 22, no. 2, pp 434-439 (2007)]. In this study, 2 tablets were used, each one containing 0.75 mg of LNG (known, for example, by the trade name Postinor-2). Meloxicam was used at a dose of 15 mg. In the group of patients who had received the combination of meloxicam and LNG, there was a trend toward a reduced incidence of ovulation compared to the group treated exclusively with LNG. This effect was increasingly more pronounced the later the tablets were taken relative to the ovulation.

The object of this invention is therefore to make available a pharmaceutical composition for emergency contraception which can be administered just once, with a reduced dose both of COX inhibitors and also of gestagen, and which at the same time shows improved contraceptive efficacy compared to the currently available gestagen-based contraceptive products. A further object of the invention is to make available products which permit safe one-off use with reduced side effects and in which, in addition, COX inhibitors are used which pose a minimal risk, or no risk, of cardiac and/or renal effects.

This object is achieved by the present invention. It was found that COX inhibitors potentiate the effect of gestagens, as a result of which the dose of gestagen required to avoid ovulation can surprisingly be considerably reduced. Conversely, gestagens can further potentiate the ovulation-inhibiting effects of COX inhibitors. By means of these synergistic effects, it is possible, despite quite a low dosage, especially of the gestagen, to achieve a comparable or even enhanced contraceptive effect and at the same time to reduce the side effects of both classes of substances.

Gestagen-associated side effects in particular (such as nausea and headaches) can be reduced by addition of the COX inhibitor, which increases the tolerability and acceptance of the method.

It was also possible to show that the use of COX inhibitors also reduces the rate of fertilization of ovulated cumulus-oocyte complexes (oocytes that are surrounded by cumulus cells, where the cumulus cells surrounding the oocyte have important functions in fertilization, Tamba S. et al. PNAS 2008). That is to say, even if the ovulation is not suppressed by COX inhibitors, there is a further contraceptive effect resulting from a reduced rate of fertilization. This is probably due to influences on the characteristics of the cumulus expansion which occurs after the LH peak and in which prostaglandins play a role (see Example 3). This leads to improved reliability of contraception compared to the LNG-based market products that only use the mechanism of ovulation inhibition. Thus, improved efficiency of contraception is achieved despite ovulation. Concerning the effect of prostaglandins on fertility, reference is made to the article by Normann R. J. THE LANCET 2001 and Sirois J. et al. Human Reproduction Update, 2004.

It is also possible in principle to divide the dose of active substances (gestagen and COX inhibitor) in equal parts to 2 pills without significantly impairing the efficacy, as long as it is ensured that the interval between the first dose and the second dose does not exceed 12 hours, and as long as it is also ensured that both pills are taken within a period of 72 hours after unprotected sex. However, for the reasons mentioned in paragraph 24 (compliance in taking the second dose, and convenience for the patient), this form of administration is not preferred.

As gestagen, it is possible in principle to use the gestagens that are known and used in oral contraceptives and also other gestagens suitable for oral use, e.g. chlormadinone acetate (CMA), norgestimate (NGM), norelgestromin (NGMN), norethisterone (NET)/norethisterone acetate (NETA), etonogestrel (3-keto-desogestrel), nomegestrol acetate (NOMAc), demegestone, promegestone, drospirenone (DRSP), medroxyprogesterone acetate (MPA), cyproterone acetate (CPA), trimegestone (TMG), levonorgestrel (LNG), norgestrel (NG), desogestrel (DSG), gestodene (GSD) or dienogest (DNG), of which levonorgestrel (LNG), desogestrel (DSG), gestodene (GSD) and dienogest (DNG) are preferred. For the use according to the invention as a product for emergency contraception, levonorgestrel is particularly preferred.

The lower dose limit for the gestagen used for the emergency contraception is a dose that still inhibits ovulation. This dose varies depending on the gestagen used. The following suggested minimal doses for inhibition of ovulation (21-day use) are found in the literature (Table 1):

TABLE 1

| Gestagen | p.o. dose/day |
| --- | --- |
| Chlormadinone acetate (CMA) | 1.5-2 mg[33], 5 mg[30] |
| Cyproterone acetate (CPA) | 1 mg[33] |
| Desogestrel (DSG) | 60 µg[28] |
| Dienogest (DNG) | 1-2 mg[29] |
| Drospirenone (DRSP) | 2 mg[33] |
| Dydrogesterone | >30 mg[33] |
| Ethynodiol | 2 mg33 |
| Gestodene (GSD) | 30 µg[33], 40-50 µg[28] |
| Levonorgestrel (LNG) | 50 µg[33], 60 µg[28] |
| Lynestrenol | 2 mg[33] |
| Medrogestone | 10 mg[33] |
| Medroxyprogesterone acetate (MPA) | 10 mg[33] |
| Nomegestrol acetate (NOMAc) | 2.5 mg[32] |
| Norethisterone | 0.5 mg[33] |
| Norethisterone acetate (NETA) | 0.5 mg[33] |
| Norgestimate (NGM) | 180-250 µg[31] |
| Progesterone | 300 mg[33] |
| Promegestone | 0.5 mg[33] |
| Trimegestone | 0.5 mg[33] |

The upper dose limit for single administration of levonorgestrel is 900 µg. According to the invention, a dose of 750 µg is preferred, i.e. an amount corresponding to half the dosage used in the emergency contraception products on the market today, which are also all based on LNG.

For the other gestagens used according to the invention, the following amounts indicate the dose ranges for preferred single administration:

TABLE 2

| | Dose p.o. (mg) | |
| --- | --- | --- |
| Gestagen | Minimum | Maximum |
| Chlormadinone acetate (CMA) | 1.5 | 75 |
| Cyproterone acetate (CPA) | 1 | 15 |
| Desogestrel (DSG) | 0.06 | 0.9 |
| Dienogest (DNG) | 1 | 30 |
| Drospirenone (DRSP) | 2 | 30 |
| Dydrogesterone | 30 | 450 |
| Ethynodiol | 2 | 30 |
| Gestodene (GSD) | 0.03 | 0.75 |
| Levonorgestrel (LNG) | 0.05 | 0.9 |
| Lynestrenol | 2 | 30 |
| Medrogestone | 10 | 150 |
| Medroxyprogesterone acetate (MPA) | 10 | 150 |
| Nomegestrol acetate (NOMAc) | 2.5 | 37 |
| Norethisterone | 0.5 | 8 |
| Norethisterone acetate (NETA) | 0.5 | 8 |
| Norgestimate (NGM) | 0.18 | 3.7 |
| Progesterone | 300 | 4500 |
| Promegestone | 0.5 | 8 |
| Trimegestone | 0.5 | 8 |

According to the invention, dose ranges are particularly preferred that correspond to twice the amount to six times the amount of an ovulation-inhibiting dose. Therefore, according to the invention, particularly preferred dose ranges are 100-360 µg for levonorgestrel, 1-12 mg for dienogest, 120-360 µg for desogestrel, 60-300 µg for gestodene, 3-30 mg for CMA, 360-1500 µg for NGM, and 5-15 mg for NOMAc.

Particular preference is given to a composition for emergency contraception which, in addition to the COX inhibitor, contains levonorgestrel in an amount of 150-300 µg.

The COX inhibitors that are used according to the invention include in principle all the COX inhibitors that are available for other indications, e.g. also meloxicam. COX inhibitors that are particularly suitable according to the invention include piroxicam, naproxen, celecoxib, diclofenac, tenoxicam, nimesulide, lornoxicam and indomethacin, of which piroxicam is particularly preferred. Thus, this COX inhibitor in combination with a gestagen (LNG) has a better effect than is achieved, for example, for the combination of LNG with meloxicam (see Example 1), and it additionally reduces fertilization.

For the COX inhibitors too, different dosages are to be employed depending on the COX inhibitor used. Dose ranges for the COX inhibitors used according to the invention result from the recommended maximum daily doses of the respective COX inhibitor for preferably single administration. These recommended maximum doses relate to long-term treatments and continuous therapies, and therefore, for the present indication of emergency contraception with preferably a single administration, it is also possible to use three times the recommended maximum daily dose. A quarter of the recommended maximum daily dose is regarded as the lower limit. For the COX inhibitors used according to the invention, this gives the following amounts (Table 3):

TABLE 3

|  | Recommended maximum daily dose* (mg) | Range for emergency contraception (mg) |
|---|---|---|
| Piroxicam | 20 | 5-60 |
| Tenoxicam | 40 | 10-120 |
| Naproxen | 1250 | 300-3800 |
| Diclofenac | 150 | 40-450 |
| Indomethacin | 200 | 50-600 |
| Celecoxib | 400 | 100-1200 |
| Nimesulide | 200 | 50-600 |
| Lornoxicam | 16 | 4-48 |
| Ibuprofen | 2400** | 600-3600 |

*Maximum daily doses as per Wolters Kluver Health (Ovid SP Verlag) Drug Information Full Text
**Maximum daily dose as per pack insert In a preferred embodiment of the invention, a combination of piroxicam in a dose range of 5-60 mg and levonorgestrel in the range of 60-750 μg is used in the pharmaceutical formulation. Particular preference is given to a formulation containing 10-30 mg of piroxicam and 150 to 300 μg of LNG.

The pharmaceutical formulation can be present in a solid or liquid state, for example as a tablet, film-coated tablet or coated tablet, wafer, capsule, pill or powder. Lyophilized powder ampule formulations, which permit in situ preparation of liquid compositions, are also included. Liquid compositions can be injection solutions or infusion solutions, for example.

The preparation of the pharmaceutical formulation is familiar to an expert. The preparation of a formulation as a tablet is described in Example 4.

The efficacy of the composition according to the invention was ascertained by ovulation-inhibiting studies carried out on adult female rats with normal cycles. First, using 5 dose groups plus placebo (0.003 mg, 0.01 mg, 0.03 mg, 0.1 mg and 0.3 mg), the limit dose of levonorgestrel (LNG) was determined at which there is still no ovulation-inhibiting effect. It was found that a dose of 0.01 mg of levonorgesterel per animal (subcutaneous, hereinafter abbreviated to s.c.) still has no ovaulation-inhibiting effect.

With the dose of LNG thus determined (0.01 mg), a comparison test was then carried out in which the ovulation-inhibiting effect of LNG, placebo, meloxicam, piroxicam, and the combination of LNG and meloxicam, was compared against the composition, according to the invention, of LNG plus piroxicam.

With the onset of the metestrus, 5 animals in each case were treated on four successive days with (a) placebo, (b) 0.01 mg of LNG, (c) 2 mg of piroxicam, (d) 0.01 mg of LNG and 2 mg of piroxicam, (e) 2 mg of meloxicam, and (f) 0.1 mg of LNG and 3 mg of meloxicam. LNG was given by s.c. administration, and the COX inhibitor was given orally (p.o.).

Whereas 42 oocytes ovulated in control group (a) and 35 oocytes ovulated in treatment group (b) with 0.1 mg of levonorgestrel, the ovulation rate with a combination of 2 mg p.o. of piroxicam plus 0.1 mg of levonorgestrel (treatment group d) was only 3 oocytes (only one animal of 5 showed any ovulation at all). By contrast, with 2 mg of piroxicam on its own (treatment group c), 9 oocytes ovulated.

At a still lower dose of just 1 mg of piroxicam, the ovulation rate for the combination with 0.1 mg of levonorgestrel was 16 oocytes, whereas 1 mg of piroxicam allowed 28 oocytes to ovulate.

The comparison between LNG/meloxicam and LNG/piroxicam and LNG shows that meloxicam plus LNG in this direct comparison is less effective than piroxicam plus LNG. Thus, a combination of 2 mg of meloxicam plus 0.01 mg of levonorgestrel still showed an ovulation rate of 18 oocytes in 5 animals.

In another test (Example 2) on rats (n=10 animals) with intact menstrual cycles, it was surprisingly found that piroxicam on its own has a significant dose-dependent effect on the serum progesterone concentration on the evening (19.00 h) of the proestrus, i.e. at the time of the LH peak. This can be seen as an indicator of the efficiency of the LH peak in changing from a predominantly estrogen-producing ovary (before the LH peak) to a predominantly progesterone-producing ovary (caused by the LH peak). This surprising finding shows that piroxicam on its own has an effect on the hormonal situation, which can result in a contraceptive effect or in an increase of a contraceptive effect of a gestagen. By contrast, the literature describes that other COX inhibitors have no effect on the hormonal levels [Pall et al.; Human Reproduction vol. 16, no. 7, pp 1323-1328 (2001); Bata et al., J Clin Pharmacol (2006) 46:925-932]. In this test too, it was found that the combination of low-dose levonorgestrel (0.01 mg s.c.) with piroxicam (0.5; 1 and 2 mg p.o.) inhibits ovulation considerably better than each substance on its own: 100 oocytes ovulated in the vehicle group, 68 in the group with LNG on its own, 85 in the group with 0.5 mg of piroxicam, 56 in the group with 1 mg of piroxicam, and 30 in the group with 2 mg of piroxicam. The ovulation rates in the combination with 0.01 mg of levonorgestrel and 0.5 mg of piroxicam (31 oocytes), with 1 mg of piroxicam (19 oocytes) and with 2 mg of piroxicam (0 oocytes) were much lower here and, in the highest dose, even led to complete anovulation (10 animals per group).

The invention is explained by the following nonlimiting examples.

EXAMPLE 1

Ovulation Inhibition Test on Rats

The rat is an especially suitable animal model for demonstration of ovulation-inhibiting substances, since it ovulates spontaneously and the menstrual cycle can be easily monitored using vaginal smears.

In the following test, female rats weighing between 200 and 220 g were used. The animals were housed in macrolon cages in rooms under controlled lighting conditions (12 hours of darkness, 12 hours of light), were fed a standard diet and had access to water ad libitum.

Levonorgestrel was dissolved in benzyl benzoate/castor oil (1+4 v/v), and the daily dose was given by s.c. administration in a volume of 1 ml/kg body weight.

The COX inhibitors were suspended in a carrier liquid (85 mg of MyrjR53 (2-hydroxyethyl octadecanoate; CAS no. 9004-99-3) in 100 ml of 0.9% w/v NaCl solution), and the daily dose corresponding to the treatment group was administered orally in a volume of 2 ml/kg body weight.

Two cycles were monitored using vaginal smears before the start of the test. Only animals with a regular 4-day cycle were entered in the test. The allocation to the treatment groups was randomized. Starting in the metestrus, the test substance was administered for 4 days (days 1-4) and the cycle continued to be monitored. On day 3 of treatment (proestrus), a retrobulbar blood sample was taken at 9.00 h and from 18.30 h in order to determine the luteinizing hormone (LH). On day 4 (after administration), the animals with vaginal smears showing them in estrus or metestrus underwent unilateral ovariectomy under anaesthetic. Crush preparations were made from the tubes and were examined under a microscope for the presence of oocytes. On day 5, all the animals (the intact animals and those having undergone unilateral ovariectomy) were sacrificed, and the tubes of the animals in estrus and metestrus were prepared and examined in the same way. The tests that were carried out show that a low dose of levonorgestrel, although not itself inhibiting ovulation, does provide increased suppression of ovulation when combined with COX inhibitors, and, in the case of piroxicam, almost complete suppression of ovulation can be achieved. By contrast, the COX inhibitors on their own provide only partial suppression of ovulation.

The results of the study, i.e. the combined effect of levonorgestrel plus COX inhibitors on ovulation, are summarized in Table 4:

TABLE 4

| Treatment group | Ovulation count, absolute | Ovulation count, mean |
|---|---|---|
| Vehicle | 42 | 8.4 ± 0.5 |
| LNG 0.01 mg s.c. | 35 | 7.0 ± 2.0 |
| Meloxicam 2 mg p.o. | 28 | 5.6 ± 2.5 |
| Piroxicam 2 mg p.o. | 9 | 1.8 ± 0.4 |
| LNG (0.01 mg) + Priox (2 mg) | 3 | 0.6 ± 1.3 (only 1 animal ovulated 3 oocytes) |
| LNG (0.01 mg) + Melox (2 mg) | 18 | 3.6 ± 3.3 |

EXAMPLE 2

The test set-up corresponds to the one described in Example 1.

The results for the progesterone concentrations in proestrus at 19.00 h are summarized in Table 5:

TABLE 5

| Treatment group | Progesterone in proestrus at 19.00 h—mean ± SD (n = 10) |
|---|---|
| Vehicle | 254 ± 88 |
| Piroxicam 0.5 mg p.o. | 237 ± 49 |
| Piroxicam 1 mg p.o. | 183 ± 67 |
| Piroxicam 2 mg p.o. | 122 ± 94 |

EXAMPLE 3

Substances can influence fertility by reducing the fertilizability of oocytes or cumulus-oocyte complexes. In order to investigate such effects, substances can be administered in vivo and, after ovulation from cumulus/oocyte complexes, can be subjected to in vitro fertilization. The in vitro fertilization rate, with no further test substance being added, allows conclusions to be drawn regarding the in vivo effects of the test substances.

Immature female mice (strain: B6D2F1, Charles River, Suelzfeld, age: 19-25 days) were housed in macrolon cages in rooms under controlled lighting conditions (12 hours of darkness, 12 hours of light), were fed a standard diet and had access to water ad libitum. The mice were primed with PMSG (Pregnant Mare Serum Gonadotropin) (10 IU/animal i.p.). After 48 hours, an ovulation-triggering stimulus was induced in the animals by administration of 10 IU/animal i.p. The COX inhibitors were suspended in a carrier liquid (85 mg MyrjR53 (2-hydroxyethyl octadecanoate; CAS no. 9004-99-3) in 100 ml of 0.9% w/v NaCl solution), and the daily dose corresponding to the treatment group (n=5 animals per group) was administered in a volume of 0.2 ml p.o. 8 hours before and together with hCG. Fourteen hours after hCG administration, the animals were sacrificed. Ovulated oocytes and cumulus-oocyte complexes were recovered from the ovarian bursa and/or oviduct and subjected to in vitro fertilization, with a sperm count of 40,000 sperm/0.5 ml for 1 hour being used for the fertilization. Twenty-four hours after incubation with the sperm, the number of fertilized oocytes was established and the percentage fertilization rate determined.

The results show that piroxicam has an effect on the fertilizability of ovulated cumulus-oocyte complexes.

The results of the study of the effect of piroxicam on the fertilization rate of ovulated cumulus-oocyte complexes are summarized in Table 6:

TABLE 6

| Treatment group | Fertilization rate (% ± SD) |
|---|---|
| Vehicle | 55 ± 16 |
| Piroxicam (2 × 0.5 mg/animal p.o.) | 12 ± 7 |
| Piroxicam (2 × 0.3 mg/animal p.o.) | 14 ± 18 |
| Piroxicam (2 × 0.15 mg/animal p.o.) | 19 ± 8 |

EXAMPLE 4

Method for Producing a Tablet for Emergency Contraception

Tablets having a total weight of 200 mg per tablet and being of the composition shown in Table 7

TABLE 7

| Levonorgestrel, micronized | 0.25 mg |
| Piroxicam, micronized | 20.00 mg |
| Lactose monohydrate | 107.75 mg |
| Maize starch | 36.00 mg |
| Modified starch | 24.00 mg |
| Polyvinylpyrrolidone 25000 | 10.00 mg |
| Magnesium stearate | 2.00 mg | were produced by filling a fluidized bed granulator with 31.68 kg of maize starch, 21.12 kg of modified starch, 0.22 kg of levonorgestrel (micronized), 17.6 kg of piroxicam (micronized) and 94.82 kg of lactose monohydrate and by activating the fluidized bed. An aqueous solution of 8.8 kg of polyvinylpyrrolidone 25000 in 50 kg of purified water was sprayed continuously onto the fluidized bed, and the mixture was dried at the same time by heating the air stream of the fluidized bed. At the end of the process, 1.76 kg of magnesium stearate were introduced into the fluidized bed granulator and mixed with the resulting granules with the fluidized bed running. The granulate thus formed was pressed in a rotary tablet press into the shape of a tablet with an 8 mm diameter.

LITERATURE

1. Swahn M L. Effect of post-coital contraceptive methods on the endometrium and the menstrual cycle. *Acta Obstet Gynecol Scand* 1996; 75:738-44.
2. Ling W Y. Mode of action of dl-norgestrel and ethinylestradiol combination in postcoital contraception. *Fertil Steril* 1979; 32:297-302.
3. Rowlands S. A possible mechanism of action of danazol and an ethinylestradiol/norgestrel combination used as postcoital contraceptive agents. *Contraception* 1986; 33:539-45.
4. Croxatto H B. Effects of the Yuzpe regimen, given during the follicular phase, on ovarian function. *Contraception* 2002; 65:121-8.
5. Kubba A A. The biochemistry of human endometrium after two regimens of postcoital contraception: a dl-norgestrel/ethinylestradiol combination or danazol. *Fertil Steril* 1986:45:512-6.
6. Ling W Y. Mode of action of dl-norgestrel and ethinylestradiol combination in postcoital contraception. II. Effect of postovulatory administration on ovarian function and endometrium. *Fertil Steril* 1983; 39:292-7.
7. Yuzpe A A. Post coital contraception—a pilot study. *J Reprod Med* 1974; 13:53-8.
8. Taskin O. High doses of oral contraceptives do not alter endometrial α1 and αvβ3integrins in the late implantation window. *Fertil Steril* 1994; 61:850-5.
9. Raymond E G. Effect of the Yuzpe regimen of emergency contraception on markers of endometrial receptivity. *Hum Reprod* 2000; 15:2351-5.
10. Ling W Y. Mode of action of dl-norgestrel and ethinylestradiol combination in postcoital contraception. III. Effect of preovulatory administration following the luteinizing hormone surge on ovarian steroidogenesis. *Fertil Steril* 1983; 40:631-6.
11. Croxatto H B. Mechanism of action of hormonal preparations used for emergency contraception: a review of the literature. *Contraception* 2001; 63:111-21.
12. Croxatto H B. Mechanisms of action of emergency contraception. *Steroids* 2003; 68:1095-8. 5
13. Glasier A. Emergency postcoital contraception. *N Engl J Med* 1997; 337:1058-64.
14. Trussell J, Raymond E G. Statistical evidence concerning the mechanism of action of the Yuzpe regimen of emergency contraception. *Obstet Gynecol* 1999; 93:872-6.
15. Hapangama D. The effects of peri-ovulatory administration of levonorgestrel on the menstrual cycle. *Contraception* 2001; 63:123-9.
16. Durand M. On the mechanisms of action of short-term levonorgestrel administration in emergency contraception. *Contraception* 2001; 64:227-34.
17. Marions L. Emergency contraception with mifepristone and levonorgestrel: mechanism of action. *Obstet Gynecol* 2002; 100:65-71.
18. Marions L, Cekan S Z, Bygdeman M, Gemzell-Danielsson K. Effect of emergency contraception with levonorgestrel or mifepristone on ovarian function. *Contraception* 2004; 69:373-7.
19. Croxatto H B. Pituitary-ovarian function following the standard levonorgestrel emergency contraceptive dose or a single 0.75-mg dose given on the days preceding ovulation. *Contraception* 2004; 70:442-50.
20. Okewole I A. Effect of single administration of levonorgestrel on the menstrual cycle. *Contraception* 2007; 75:372-7.
21. Durand M. Late follicular phase administration of levonorgestrel as an emergency contraceptive changes the secretory pattern of glycodelin in serum and endometrium during the luteal phase of the menstrual cycle. *Contraception* 2005; 71:451-7.
22. Nascimento J A. In vivo assessment of the human sperm acrosome reaction and the expression of glycodelin-A in human endometrium after levonorgestrel emergency contraceptive pill administration. *Hum Reprod* 2007; 22:2190-5.
23. Kesserü E. The hormonal and peripheral effects of dnorgestrel in postcoital contraception. *Contraception* 1974; 10:411-24.
24. Trussell J. Plan B and the politics of doubt. *J Am Med Assoc* 2006; 296:1775-8.
25. Müller A L. Postcoital treatment with levonorgestrel does not disrupt postfertilization events in the rat. *Contraception* 2003; 67:415-19.
26. Ortiz M E. Postcoital administration of levonorgestrel does not interfere with post-fertilization events in the new-world monkey Cebus apella. *Hum Reprod* 2004; 19:1352-6.
27. Hatcher R A, Trussell J. *Emergency Contraception: The Nation's Best Kept Secret*. Decatur Ga.: Bridging the Gap Communications, 1995.
28. Teichmann "Empfängnishütung: eine vergleichende Übersicht aller Methoden, Risiken and Indikationen", published by Georg Thieme Verlag (1996)
29. Moore C, Carol W, Gräser T et al. in Clin Drug Invest 18, 271-8 (1999) Influence of dienogest on ovulation in young fertile women
30. R. Druckmann; contraception 79 (2009) 272-281: Profile of progesterone derivative chlormadinone acetate—Pharmacodynamic properties and therapeutic applications
31. Fertility control Stephen L. Corson, Richard J. Derman, Louise B. Tyrer Edition: 2, illustrated. Publishers Taylor & Francis, 1994 ISBN 096979780X, 9780969797807 514 pages
32. Bazin B, Thevenot R, Bursaux C and Paris J (1987) Effect of nomegestrol acetate, a new 19 nor-progesterone derivative, on pituitary-ovarian function in women. Br J Obstet Gynaecol 94, 1199-1204
33. Schindler A. E. et al (2003) Classification and pharmacology of progestins Maturitas 46, S1, 7-16

The invention claimed is:
1. A pharmaceutical composition, comprising
 (a) 50-900 µg levonorgestrel,
 (b) a COX inhibitor selected from: 50-600 mg indomethacin and 40-50 mg diclofenac; and
 (c) a pharmaceutically acceptable excipient,
 wherein the pharmaceutical composition is adapted for oral emergency contraception in a single dose to prevent pregnancy.
2. The pharmaceutical composition as claimed in claim 1, characterized in that the levonorgestrel is in a range of 100-360 µg.
3. The pharmaceutical composition as claimed in claim 1, wherein the levonorgestrel is in a range of 150-300 µg.
4. A method for emergency contraception comprising administering to a patient in need thereof a composition comprising the composition of claim 1.

5. The method of claim 4, wherein the pharmaceutical composition is administered in a single dose within 72 hours post coitus.

* * * * *